United States Patent
Cho et al.

(10) Patent No.: US 10,003,102 B2
(45) Date of Patent: Jun. 19, 2018

(54) ELECTROLYTE ADDITIVE FOR LITHIUM BATTERY, ELECTROLYTE INCLUDING THE ADDITIVE, AND LITHIUM BATTERY INCLUDING THE ELECTROLYTE

(71) Applicant: SAMSUNG SDI CO., LTD., Yongin-si, Gyeonggi-do (KR)

(72) Inventors: Erang Cho, Yongin-si (KR); Duckhyun Kim, Yongin-si (KR); Moonsung Kim, Yongin-si (KR); Jeonghye Lee, Yongin-si (KR); Woocheol Shin, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 161 days.

(21) Appl. No.: 14/705,819

(22) Filed: May 6, 2015

(65) Prior Publication Data
US 2016/0020488 A1 Jan. 21, 2016

(30) Foreign Application Priority Data
Jul. 16, 2014 (KR) .................. 10-2014-0089898

(51) Int. Cl.
| | |
|---|---|
| H01M 10/0567 | (2010.01) |
| H01M 6/16 | (2006.01) |
| C07C 317/28 | (2006.01) |
| C07D 333/24 | (2006.01) |
| C07D 213/57 | (2006.01) |
| H01M 10/052 | (2010.01) |

(52) U.S. Cl.
CPC ....... H01M 10/0567 (2013.01); C07C 317/28 (2013.01); C07D 213/57 (2013.01); C07D 333/24 (2013.01); H01M 6/168 (2013.01); C07C 2601/08 (2017.05); H01M 10/052 (2013.01); H01M 2300/0025 (2013.01)

(58) Field of Classification Search
CPC .......... H01M 10/0567; H01M 10/052; H01M 6/168; C07C 317/28; C07D 213/57; C07D 333/24
See application file for complete search history.

(56) References Cited

U.S. PATENT DOCUMENTS

| | | | | |
|---|---|---|---|---|
| 4,412,942 A | * | 11/1983 | Naarmann ................ | C08F 8/42 252/512 |
| 7,767,343 B2 | | 8/2010 | Abe et al. | |
| 2013/0337317 A1 | | 12/2013 | Shima et al. | |

FOREIGN PATENT DOCUMENTS

| | | |
|---|---|---|
| JP | 2002-134168 A | 5/2002 |
| JP | 2012-056925 A | 3/2012 |
| JP | 2012-134137 A | 7/2012 |
| JP | 2012-190791 A | 10/2012 |

OTHER PUBLICATIONS

Leusen et al. "Chemistry of sulfonylmethyl isocyanides. 10. Phase-transfer mono-alkylation of p-tolylsulfonylmethylisocyanide"; Tetrahedron Letters (1975), (40), pp. 3487-3488.*
Sisko et al. "α-Tosylbenzyl isocyanide"; Organic Syntheses (2000), 77, pp. 198-205.*
Patent Abstracts of Japan and English Machine Translation of Japanese Publication No. 2002-134168 A, May 10, 2002, 17 Pages.
Patent Abstracts of Japan and English Machine Translation of Japanese Publication No. 2012-056925 A, Mar. 22, 2012, 16 Pages.
Patent Abstracts of Japan and English Machine Translation of Japanese Publication No. 2012-134137 A, Jul. 12, 2012, 101 Pages.

* cited by examiner

*Primary Examiner* — Laura Weiner
(74) *Attorney, Agent, or Firm* — Lewis Roca Rothgerber Christie LLP

(57) ABSTRACT

An electrolyte additive for a lithium battery, an electrolyte including the electrolyte additive, and a lithium battery including the electrolyte additive are disclosed. The electrolyte additive for a lithium battery includes a sulfonylmethylisocyanide-based compound. The electrolyte additive including the sulfonylmethylisocyanide-based compound may form a protective layer having improved high-temperature stability on positive and negative electrodes of a lithium battery, thereby improving the safety of the lithium battery.

8 Claims, 5 Drawing Sheets

ELECTROLYTE ADDITIVE FOR LITHIUM BATTERY, ELECTROLYTE INCLUDING THE ADDITIVE, AND LITHIUM BATTERY INCLUDING THE ELECTROLYTE

RELATED APPLICATION

This application claims priority to and the benefit of Korean Patent Application No. 10-2014-0089898, filed on Jul. 16, 2014, in the Korean Intellectual Property Office, the entire content of which is incorporated herein by reference.

BACKGROUND

1. Field

One or more embodiments of the present invention relate to an electrolyte additive for a lithium battery, an electrolyte including the electrolyte additive, and a lithium battery including the electrolyte.

2. Description of the Related Art

With the advances in the field of small high-tech devices such as digital cameras, mobile devices, laptops, and personal computers, there has been a sharp increase in demand for lithium batteries as energy sources. Also, with the spread of electric vehicles, safe lithium batteries for electric vehicles are under development.

Lithium batteries operate at a high driving voltage because they have a higher energy density per unit weight than those of comparable lead storage batteries, nickel-cadmium (Ni—Cd) batteries, nickel-hydrogen batteries, and nickel-zinc batteries. Such lithium batteries cannot be used safely or effectively with an aqueous electrolyte having high reactivity to lithium, and thus a nonaqueous organic electrolyte is used together with a polar aprotic organic solvent for the nonaqueous organic electrolyte.

The nonaqueous organic electrolyte may be decomposed by reacting with a negative or positive electrode during charging and/or discharging, or may be spontaneously, thermally decomposed. The decomposition of the nonaqueous organic electrolyte may cause heat generation in a battery or even an explosion of the battery, which may occur when the amount of released heat is smaller than the amount of generated heat. Such a situation may occur more frequently (or may be more likely to occur) in larger batteries.

SUMMARY

One or more embodiments of the present invention include an electrolyte additive for a lithium battery, the electrolyte additive being capable of improving safety of a lithium battery.

One or more embodiments of the present invention include an electrode including the electrolyte additive.

One or more embodiments of the present invention include a lithium battery including the electrolyte.

Additional aspects will be set forth in part in the description which follows and, in part, will be apparent from the description, or may be learned by practice of the presented embodiments.

According to one or more embodiments of the present invention, an electrolyte additive for a lithium battery includes a sulfonylmethylisocyanide-based compound represented by Formula 1:

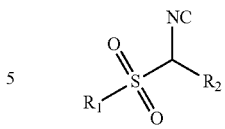

Formula 1

In Formula 1, $R_1$ may be a substituted or unsubstituted C1-C20 alkyl group; C1-C20 alkoxy group; C2-C20 alkenyl group; C2-C20 alkenyloxy group; C4-C20 cycloalkyl group; C4-C20 cycloalkenyl group; C2-C20 alkynyl group; or C6-C20 aryl group, and $R_2$ may be a substituted or unsubstituted aliphatic, alicyclic, or aromatic hydrocarbon group.

$R_1$ may be a substituted or unsubstituted C6-C20 aryl group.

The aliphatic hydrocarbon group may be a C1-C20 alkyl group, a C1-C20 alkoxy group, a C2-C20 alkenyl group, a C2-C20 alkenyloxy group; or a C2-C20 alkynyl group, the alicyclic hydrocarbon group may be a C4-C20 cycloalkyl group; a C4-C20 cycloalkenyl group; or a C2-C20 heterocycloalkyl group, and the aromatic hydrocarbon group may be a C6-C20 aryl group or a C2-C20 heteroaryl group.

$R_2$ may be a hydrogen atom, a methyl group, an ethyl group, a propyl group, an isopropyl group, a butyl group, an isobutyl group, a tert-butyl group, a sec-butyl group, a vinyl group, an allyl group, a butenyl group, a pentenyl group, an ethynyl group, a propynyl group, a butynyl group, a pentynyl group, a cyclobutyl group, a cyclopentyl group, a cyclohexyl group, a cycloheptyl group, a phenyl group, a naphthyl group, a pyridinyl group, or a thiophenyl group.

The sulfonylmethylisocyanide-based compound may include a compound represented by Formula 3 below:

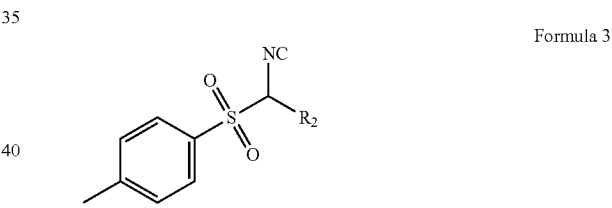

Formula 3

In Formula 3, $R_2$ is as defined with respect to Formula 1.

According to one or more embodiments of the present invention, an electrolyte for a lithium battery includes a lithium salt; a nonaqueous organic solvent; and the electrolyte additive.

An amount of the electrolyte additive in the electrolyte may be about 0.01 parts to about 10 parts by weight based on 100 parts by weight of the nonaqueous organic solvent.

According to one or more embodiments of the present invention, a lithium battery includes a positive electrode; a negative electrode; and the electrolyte.

BRIEF DESCRIPTION OF THE DRAWINGS

These and/or other aspects will become apparent and more readily appreciated from the following description of the embodiments, when considered together with the accompanying drawings in which.

DETAILED DESCRIPTION

Figure 1:
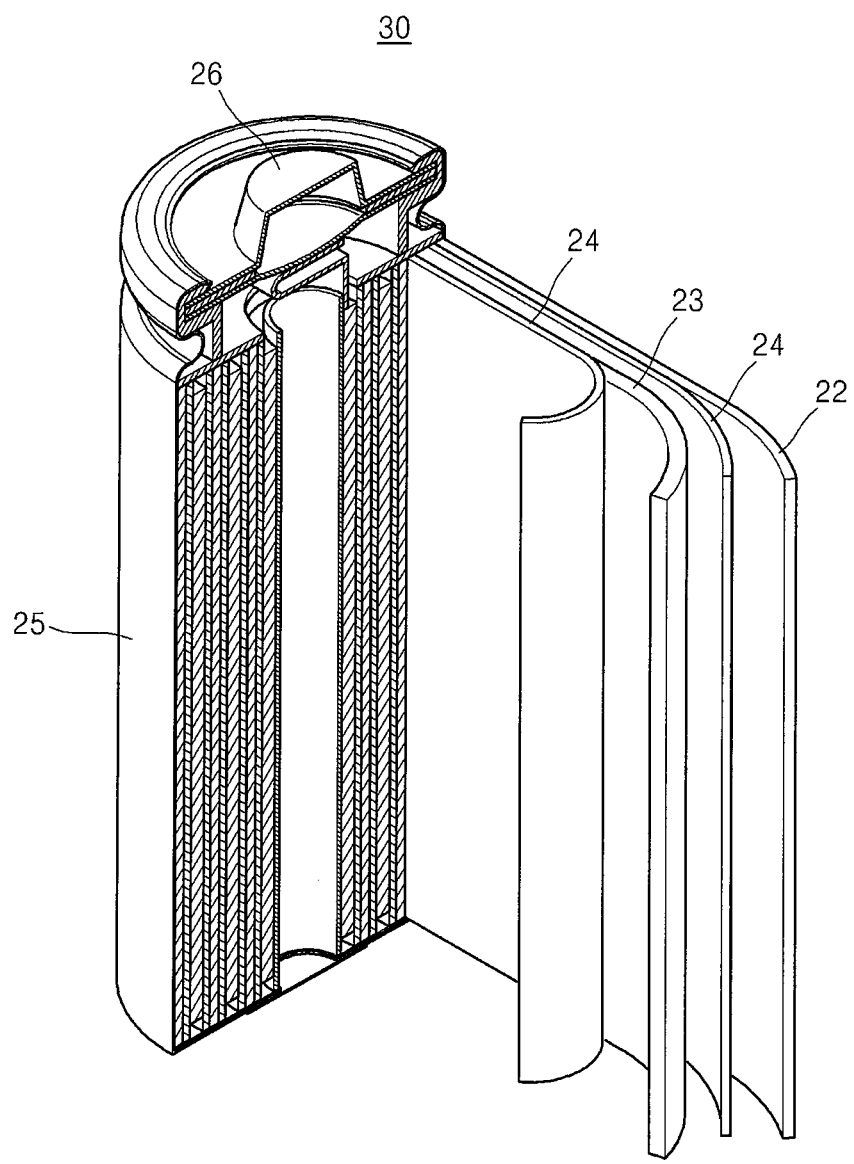
FIG. 1 is a schematic, partially exploded, perspective view of a structure of a lithium battery according to an embodiment of the present disclosure.

Reference will now be made to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are described below, by referring to the figures, merely to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention." As used herein, the terms "use," "using," and "used" may be considered synonymous with the terms "utilize," "utilizing," and "utilized," respectively.

Embodiments of the present invention address a need to develop an electrolyte additive for a lithium battery whereby a lithium battery with higher capacity and improved the safety may be obtained. According to an embodiment of the present invention, an electrolyte additive for a lithium battery includes a sulfonylmethylisocyanide-based compound represented by Formula 1 below:

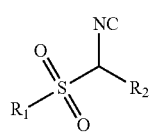

Formula 1

In Formula 1, $R_1$ may be a substituent that may be a substituted or unsubstituted C1-C20 alkyl group; C1-C20 alkoxy group; C2-C20 alkenyl group; C2-C20 alkenyloxy group; C4-C20 cycloalkyl group; C4-C20 cycloalkenyl group; C2-C20 alkynyl group; or C6-C20 aryl group, and $R_2$ may be a substituent that may be a substituted or unsubstituted aliphatic, alicyclic, or aromatic hydrocarbon group.

In general, an electrolyte for a lithium battery, for example, a lithium secondary battery, may transport lithium ions from a positive electrode to a negative electrode during charging and vice versa during discharging. When the electrolyte contacts the positive or negative electrode, oxidation-reduction decomposition of the electrolyte may occur at an interface between the two electrodes, and the resulting decomposition product may be deposited or adsorbed onto a surface of the positive or negative electrode, thereby forming an interface layer. The decomposition product may be permanently or substantially permanently adhered to the electrode and thus serve as a protective layer of a surface of the electrode, though a portion of the decomposition product may be partially desorbed or dissolved out of the interface layer. The protective layer is substantially an insulator having negligible electron conductivity, but the protective layer has a high conductivity of lithium ions, and may behave like a solid electrolyte. For this reason, the protective layer is referred to as a "solid electrolyte interphase (SEI)" layer.

The SEI layer may serve as an ion tunnel at an electrode-electrolyte interface, and may relieve concentration deviations and an overvoltage to facilitate migration of lithium ions in a uniform or substantially uniform current distribution. Once the SEI layer has been formed, the migration of electrons that induce a reaction between the electrolyte and at least one of the negative electrode and the positive electrode may be suppressed (or reduced) to thus prevent (or reduce) further decomposition of the electrolyte.

Thus, to suppress (or reduce) an exothermic reaction in a lithium battery, it is beneficial when a stable SEI layer is formed at the interface of the electrolyte. Conventionally, when an additive is included in an electrolyte to form a stable SEI layer, a capacity and/or life characteristics of a battery deteriorates in some cases. To avoid or reduce a deterioration of the life characteristics of a lithium battery, embodiments of the present invention include an additive for forming an SEI layer having high-temperature stability and an electrolyte including the additive so that the life characteristics of a lithium battery including the electrolyte do not deteriorate (or deteriorate less).

Hereinafter, embodiments of an electrolyte additive for a lithium battery will be described for a better understanding of the principles of the present invention, though the scope of the present invention is not limited to the embodiments described herein.

In the sulfonylmethylisocyanide-based compound of Formula 1, a sulfonyl group and an isocyano group are bound to a methylene group (or a methylene-based group, such as a substituted methylene group), and the compound of Formula 1 may induce a decomposition reaction of a portion of an electrolyte on a surface of a positive electrode and/or may induce a decomposition of a portion of the electrolyte on a surface of a negative electrode to form an SEI layer that is not prone to deteriorate at a high temperature. For example, the sulfonylmethylisocyanide-based compound may more easily accept electrons from a negative electrode, as compared to most polar organic solvents. In some embodiments, the sulfonylmethylisocyanide-based compound may be reduced at a voltage that is lower than a reduction voltage of a polar organic solvent, and thus the sulfonylmethylisocyanide-based compound may be reduced before the polar organic solvent is reduced. Accordingly, this may suppress (or reduce) a reduction reaction of the electrolyte at an interface of the electrode (e.g., the positive electrode and/or the negative electrode).

In the sulfonylmethylisocyanide-based compound represented by Formula 1, $R_1$ may be a substituent, and an example of the substituent may be a substituted or unsubstituted C1-C10 alkyl group; C1-C10 alkoxy group; C2-C10 alkenyl group; C2-C10 alkenyloxy group; C4-C10 cycloalkyl group; C4-C10 cycloalkenyl group; C2-C10 alkynyl group; or C6-C10 aryl group.

For example, in the sulfonylmethylisocyanide-based compound represented by Formula 1, $R_1$ may be a substituted or unsubstituted C6-C20 aryl group, or, for example, $R_1$ may be a substituted or unsubstituted C6-C10 aryl group.

When $R_1$ in Formula 1 above has a cyclic form (e.g., an aryl group), and not a chain form, $R_1$ may be directly linked to the sulfonyl group, so that a resulting SEI layer may have improved stability even after a long charge and discharge.

This may further prevent (or reduce) thermal decomposition of the electrolyte, and consequently improve the stability of the resultant lithium battery.

In the sulfonylmethylisocyanide-based compound represented by Formula 1, the aliphatic hydrocarbon group may be a C1-C20 alkyl group, a C1-C20 alkoxy group, a C2-C20 alkenyl group, a C2-C20 alkenyloxy group, or a C2-C20 alkynyl group; the alicyclic hydrocarbon group may be a C4-C20 cycloalkyl group, a C4-C20 cycloalkenyl group, or a C2-C20 heterocycloalkyl group; and the aromatic hydrocarbon group may be a C6-C20 aryl group or a C2-C20 heteroaryl group.

For example, the aliphatic hydrocarbon group may be a C1-C10 alkyl group, a C1-C10 alkoxy group, a C2-C10 alkenyl group, a C2-C10 alkenyloxy group, or a C2-C10 alkynyl group; the alicyclic hydrocarbon group may be a C4-C10 cycloalkyl group, a C4-C10 cycloalkenyl group, or a C2-C10 heterocycloalkyl group; and the aromatic hydrocarbon group may be a C6-C10 aryl group or a C2-C10 heteroaryl group.

For example, $R_2$ may be a hydrogen, a methyl group, an ethyl group, a propyl group, an isopropyl group, a butyl group, an isobutyl group, a tert-butyl group, a sec-butyl group, a vinyl group, an allyl group, a butenyl group, a pentenyl group, an ethynyl group, a propynyl group, a butynyl group, a pentynyl group, a cyclobutyl group, a cyclopentyl group, a cyclohexyl group, a cycloheptyl group, a phenyl group, a naphthyl group, a pyridinyl group, or a thiophenyl group.

In the sulfonylmethylisocyanide-based compound represented by Formula 1, the aliphatic, alicyclic, and aromatic hydrocarbon groups may be each independently substituted or unsubstituted with a substituent. The substituent may be a halogen atom; an amino group; a cyano group; a nitro group; a halogen-substituted or unsubstituted C1-C8 alkyl group; a halogen-substituted or unsubstituted C1-C8 alkoxy group; a halogen-substituted or unsubstituted C2-C8 alkenyl group; a halogen-substituted or unsubstituted C2-C8 alkenyloxy group; a halogen-substituted or unsubstituted C2-C8 alkynyl group; a halogen-substituted or unsubstituted C4-C10 cycloalkyl group; a halogen-substituted or unsubstituted C3-C10 cycloalkoxy group; a halogen-substituted or unsubstituted C4-C10 cycloalkenyl group; a halogen-substituted or unsubstituted C2-C10 heterocycloalkyl group; a halogen-substituted or unsubstituted C6-C10 aryl group; a halogen-substituted or unsubstituted C6-C10 aryloxy group; or a halogen-substituted or unsubstituted C6-C10 heteroaryl group. For example, the substituent may be at least one selected from the group consisting of a halogen atom, a methyl group, an ethyl group, a propyl group, an isopropyl group, a butyl group, a tert-butyl group, a trifluoromethyl group, a tetrafluoroethyl group, a methoxy group, an ethoxy group, a propoxy group, a phenyl group, a naphthyl group, a tetrafluorophenyl group, a pyrrolyl group, and a pyridinyl group, but the substituent is not limited thereto.

For example, the compound represented by Formula 1 above may have a resonance structure as shown in Formula 2 below:

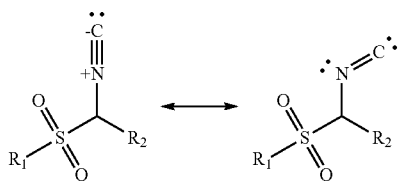

Formula 2

The resonance structure shown in Formula 2 originates from resonance (electronic resonance) of an isocyano group. As shown in Formula 2, a structure on the right having no charges in the molecule does not satisfy an octet rule, and thus a structure on the left having charges (a positive charge and a negative charge) may have a high resonance structure contribution. An isocyano group, as well as a sulfonyl group, each correspond to an electron withdrawing group, and thus a hydrogen (an α-hydrogen) located at a methylene group (or methylene-based group) between the sulfonyl group and the isocyano group, may have a high acidity. The α-hydrogen having a high acidity may be easily detached, and, in this regard, the sulfonylmethylisocyanide-based compound may be easily dissociated into radicals and/or ions during charging and discharging.

Moreover, the sulfonylmethylisocyanide-based compound has a charge (a positive charge and a negative charge) at (or within) the molecule even when the compound is in a neutral state, and thus reactivity of the compound may be better than that of a polar organic solvent. For example, the sulfonylmethylisocyanide-based compound may be reduced (or reacted) at a voltage that is lower than a reduction voltage (or a reaction voltage) of a polar organic solvent, and thus the sulfonylmethylisocyanide-based compound may be reduced on a surface of a negative electrode before the polar organic solvent is reduced as a charge voltage drops from an open-circuit voltage when the battery is charged. Accordingly, in the case of an electrolyte including the additive, a new film may be formed at an interface of the negative electrode during the first charging, and a voltage of reduction decomposition reaction of the polar organic solvent on the film changes, and thus, additional reduction of the electrolyte thereafter may be suppressed (or reduced). Due to the formation of the new film, a resistance of the battery increases, and thus stability of the battery improves, but a capacity and life characteristics of the battery may not be decreased.

For example, the sulfonylmethylisocyanide-based compound represented by Formula 1 may include a compound represented by Formula 3 below:

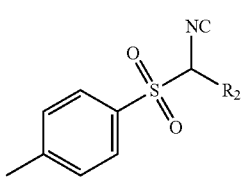

Formula 3

In Formula 3, $R_2$ is as defined with respect to Formula 1, and a p-toluenesulfonyl group may be referred to as a tosyl group that may be bound with (or react with) oxygen to form tosylate, which is a stable negative ion group. In this regard, a tosyl group may serve as a leaving group, and thus the sulfonylmethylisocyanide-based compound may be more easily decomposed into radicals and/or ions together with the dissociation of the α-hydrogen. Since the decomposition of the compound may be faster than the decomposition of the electrolyte, the sulfonylmethylisocyanide-based compound may participate in formation of an SEI layer before the other components of the electrolyte (e.g., the polar organic solvent) do. This may further prevent (or reduce) thermal decomposition of the electrolyte, and consequently improve the safety of the lithium battery.

For example, the sulfonylmethylisocyanide-based compound represented by Formula 1 may include at least one of compounds represented by Formulae 4 to 13 below:

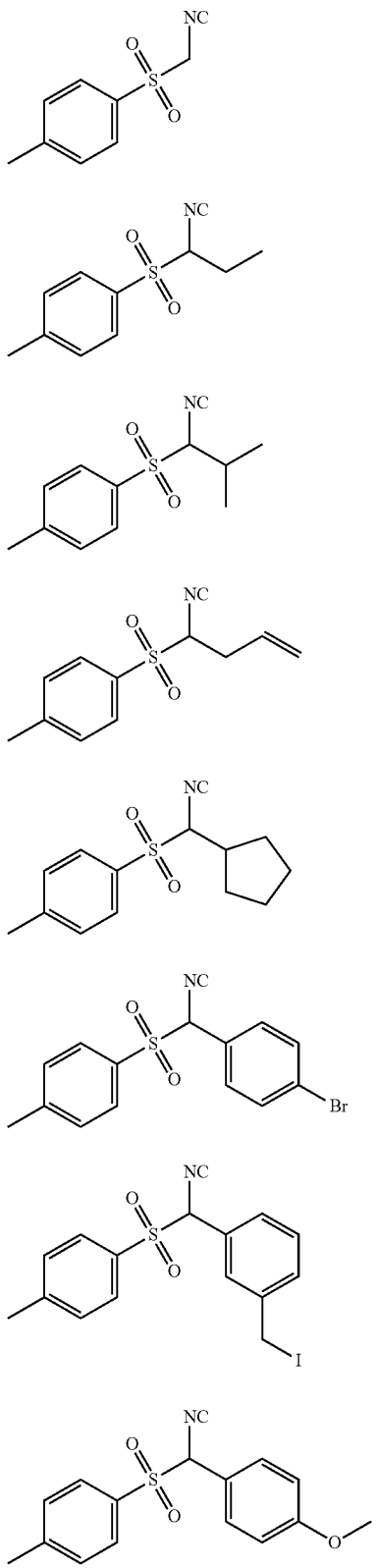

Formula 4

Formula 5

Formula 6

Formula 7

Formula 8

Formula 9

Formula 10

Formula 11

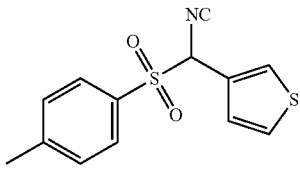

Formula 12

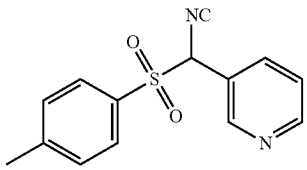

Formula 13

As used herein, the term "a radical" may refer to a mono-radical or a di-radical. For example, a substituent of a group that may have two binding sites may be construed as a bi-radical. For example, substituents of an alkyl group having two binding sites may include di-radicals, for example, —CH$_2$—, —CH$_2$CH$_2$—, and —CH$_2$CH(CH$_3$)CH$_2$—. The term for a radical such as "alkylene" may explicitly refer to a di-radical.

As used herein, the terms "alkyl group" or "alkylene group" may refer to a branched or unbranched aliphatic hydrocarbon group. In some embodiments, the alkyl group may be substituted or unsubstituted. Non-limiting examples of the alkyl group include a methyl group, an ethyl group, a propyl group, an isopropyl group, a butyl group, an isobutyl group, a tert-butyl group, a pentyl group, a hexyl group, a cyclopentyl group, a cyclohexyl group, and a cycloheptyl group, which may be each independently substituted or unsubstituted. In some embodiments, the alkyl group may have 1 to 10 carbon atoms. For example, the C1-C10 alkyl group may be a methyl group, an ethyl group, a propyl group, an isopropyl group, a butyl group, an isobutyl group, a sec-butyl group, a pentyl group, a 3-pentyl group, a hexyl group, a heptyl group, an octyl group, a nonyl group, or a dodecyl group, but the C1-C10 alkyl group is not limited thereto.

As used herein, the term "cycloalkyl group" may refer to a fully saturated carbocyclic or ring system, for example, a cyclobutyl group, a cyclopentyl group, or a cyclohexyl group.

As used herein, the term "alkenyl group" may refer to a hydrocarbon group including at least one carbon-carbon double bond. Non-limiting examples of the alkenyl group include an ethenyl group, a 1-propenyl group, a 2-propenyl group, a 2-methyl-1-propenyl group, a 1-butenyl group, and a 2-butenyl group. In some embodiments, the alkenyl group may be substituted or unsubstituted. In some embodiments, the alkenyl group may have 2 to 10 carbon atoms.

As used herein, the term "alkynyl group" may refer to a hydrocarbon group including at least one carbon-carbon triple bond. Non-limiting examples of the alkynyl group include an ethynyl group, a 1-propynyl group, a 1-butynyl group, and a 2-butynyl group. In some embodiments, the alkynyl group may be substituted or unsubstituted. In some embodiments, the alkynyl group may have 2 to 10 carbon atoms.

As used herein, the term "aromatic" may refer to a ring or a cyclic system having a conjugated π-electron system, for example, including a carbon cyclic aromatic ring and a heterocyclic aromatic ring. When the cyclic system is aromatic as a whole, the term "aromatic" may include a single ring or a fused polycyclic system (e.g., a system including a ring that shares adjacent electron pairs).

As used herein, the term "aryl group" may refer to an aromatic ring (e.g., a single aromatic ring) or cyclic system including only carbons in a backbone of the ring (e.g., at least two fused rings that share two adjacent carbon atoms). When an aryl group is a cyclic system, every ring in the cyclic system may be aromatic. Non-limiting examples of the aryl group include a phenyl group, a biphenyl group, a naphthyl group, a phenanthrenyl group, and a naphthacenyl group. The aryl group may be substituted or unsubstituted.

As used herein, the term "heteroaryl group" may refer to an aromatic cyclic system having one ring or a plurality of fused rings in which at least one cyclic atom (e.g., at least one atom of a ring) is a heteroatom (e.g., is not carbon). In the cyclic system having fused rings, only one ring may include at least one heteroatom, but the cyclic system is not limited thereto. Non-limiting examples of the heteroatoms include oxygen (O), sulfur (S), and nitrogen (N). Non-limiting examples of the heteroaryl group include a furanyl group, a thienyl group, an imidazolyl group, a quinazolinyl group, a quinolinyl group, an isoquinolinyl group, a quinoxalinyl group, a pyridinyl group, a pyrrolyl group, an oxazolyl group, and an indolyl group.

As used herein, the term "cycloalkenyl group" may refer to a carbocyclic ring or cyclic system having at least one double bond, but no aromatic ring (e.g., the carbocyclic ring or cyclic system is not aromatic). For example, the cycloalkenyl group may be a cyclohexenyl group.

As used herein, the term "heterocycloalkyl group" may refer to a nonaromatic ring or cyclic system including at least one heteroatom in a backbone of the ring.

As used herein, the term "halogen" may refer to a stable element of Group 17 of the periodic table of the elements, for example, fluorine, chlorine, bromine, or iodine. For example, the halogen may be fluorine and/or chlorine.

As used herein, the term "substituent" may refer to a resulting product of exchange of at least one hydrogen atom of an unsubstituted, mother group with another atom or functional group. When a functional group is described as being "optionally substituted" herein, it indicates that the functional group may be substituted with a substituent as described above.

According to another embodiment of the present disclosure, an electrolyte for a lithium battery includes a lithium salt, a nonaqueous organic solvent, and an electrolyte additive including an embodiment of the sulfonylmethylisocyanide-based compound according to the above-described embodiments of the present disclosure.

An amount of the sulfonylmethylisocyanide-based compound of Formula 1 present in the electrolyte as an electrolyte additive may be about 0.01 parts by weight to about 10 parts by weight based on 100 parts by weight of the nonaqueous organic solvent, but the sulfonylmethylisocyanide-based compound is not limited thereto. For example, an appropriate amount of the sulfonylmethylisocyanide-based compound of Formula 1 above may be used as is suitable. For example, the amount of the sulfonylmethylisocyanide-based compound of Formula 1 in the electrolyte may be about 0.1 parts by weight to about 5 parts by weight, and in some embodiments, about 0.1 parts by weight to about 3 parts by weight, and in some other embodiments, about 0.1 parts by weight to about 2 parts by weight, and in still other embodiments, about 0.5 parts by weight to about 2 parts by weight, each being based on 100 parts by weight of the nonaqueous organic solvent. When the amount of the sulfonylmethylisocyanide-based compound of Formula 1 in the electrolyte is within any of the foregoing ranges, an SEI layer having an appropriate (or suitable) thickness and good safety may be obtained. Accordingly, a lithium battery with improved penetration safety and increased film resistance but without significant capacity reduction may be manufactured by using the electrolyte according to embodiments of the present invention.

The lithium salt used in the electrolyte may serve as a supply source of lithium ions in the lithium battery, thereby enabling the basic operation of the lithium battery. The lithium salt may be any suitable lithium salt available in the art for use in lithium batteries, for example, a material dissolvable in any of the above-listed nonaqueous electrolytes. For example, the lithium salt may be at least one material of LiCl, LiBr, LiI, LiClO$_4$, LiB$_{10}$Cl$_{10}$, LiPF$_6$, CF$_3$SO$_3$Li, CH$_3$SO$_3$Li, C$_4$F$_9$SO$_3$Li, (CF$_3$SO$_2$)$_2$NLi, LiN(C$_x$F$_{2x+1}$SO$_2$)(C$_y$F$_{2+y}$SO$_2$) (where x and y are natural numbers), CF$_3$CO$_2$Li, LiAsF$_6$, LiSbF$_5$, LiAlCl$_4$, LiAlF$_4$, lithium chloroborate, lower aliphatic lithium carbonate, 4-phenyl lithium borate, and lithium imide.

To ensure that the lithium battery has practical (or suitable) characteristics, a concentration of the lithium salt in the electrolyte may be, for example, about 0.1M to about 2.0M. When the concentration of the lithium salt is within the foregoing range, the electrolyte may have improved performance, an appropriate (or suitable) conductivity and viscosity, and may ensure effective migration of lithium ions.

The nonaqueous organic solvent used in the electrolyte may serve as a migration medium of ions involved in electrochemical reactions in the lithium battery. For example, the nonaqueous organic solvent may include a carbonate-based compound, an ester-based compound, an ether-based compound, a ketone-based compound, an alcohol-based compound, an aprotic solvent, or a combination thereof.

The carbonate-based compound may be a chain carbonate compound (e.g., a linear or branched carbonate compound), a cyclic carbonate compound, a chain fluorocarbonate compound (e.g., a linear or branched carbonate compound), a cyclic fluorocarbonate compound, or a combination thereof.

Non-limiting examples of the chain carbonate compound include diethyl carbonate (DEC), dimethyl carbonate, (DMC), dipropyl carbonate (DPC), methyl propyl carbonate (MPC), ethyl propyl carbonate (EPC), methyl ethyl carbonate (MEC), and a combination thereof.

Non-limiting examples of the cyclic carbonate compound include ethylene carbonate (EC), propylene carbonate (PC), butylene carbonate (BC), vinyl ethylene carbonate (VEC), and a combination thereof.

Non-limiting examples of the chain or cyclic fluorocarbonate compound include fluoroethylene carbonate (FEC), 4,5-difluoroethylene carbonate, 4,4-difluoroethylene carbonate, 4,4,5-trifluoroethylene carbonate, 4,4,5,5-tetrafluoroethylene carbonate, 4-fluoro-5-methylethylene carbonate, 4-fluoro-4-methylethylene carbonate, 4,5-difluoro-4-methylethylene carbonate, 4,4,5-trifluoro-5-methylethylene carbonate, trifluoromethylethylene carbonate, and a combination thereof.

The nonaqueous organic solvent may include a mixture of the chain carbonate compound and the cyclic carbonate compound. For example, when an amount of the cyclic carbonate compound in the nonaqueous organic solvent is at least about 5 vol % based on a total volume of the nonaqueous organic solvent, cycle characteristics may be remarkably improved. For example, the amount of the cyclic carbonate compound in the nonaqueous organic solvent may be about 5 vol % to about 50 vol % based on the total volume of the nonaqueous organic solvent. When the amount of the cyclic carbonate compound is within any of the foregoing ranges, the cyclic carbonate compound may have a specific dielectric constant of about 20 or greater to facilitate dissociation of the lithium salt, thereby further increasing the ion conductivity of the electrolyte.

The carbonate-based compound may include a mixture of the chain and/or cyclic carbonate compound and further include a fluorocarbonate compound. The fluorocarbonate compound may increase the solubility of the lithium salt to improve the ion conductivity of the electrolyte, and may facilitate formation of a film on the negative electrode. In some embodiments, the fluorocarbonate compound may be FEC. An amount of the fluorocarbonate compound in the nonaqueous organic solvent may be about 1 vol % to about 30 vol % based on the total volume of the nonaqueous organic solvent. When the amount of the fluorocarbonate compound is within the foregoing range, a desired effect may be achieved due to an appropriate (or suitable) viscosity of the nonaqueous organic solvent. In some embodiments, the carbonate-based compound may further include VEC, together with the FEC. For example, an amount of the VEC in the nonaqueous organic solvent may be about 0.1 vol % to about 10 vol % based on the total volume of the nonaqueous organic solvent.

Non-limiting examples of the ester-based compound include methyl acetate, ethyl acetate, n-propyl acetate, dimethyl acetate, methyl propionate (MP), ethyl propionate, γ-butyrolactone, decanolide, valerolactone, mevalonolactone, caprolactone, and methyl formate. Non-limiting examples of the ether-based compound include dibutyl ether, tetraglyme, diglyme, 1,2-dimethoxyethane, 1,2-diethoxyethane, ethoxymethoxyethane, 2-methyltetrahydrofuran, and tetrahydrofuran. A non-limiting example of the ketone-based compound includes cyclohexanone. Non-limiting examples of the alcohol-based compound include ethyl alcohol and isopropyl alcohol.

Non-limiting examples of the aprotic solvent include dimethyl sulfoxide, 1,2-dioxolane, sulfolane, methyl sulfolane, 1,3-dimethyl-2-imidazolidinone, N-methyl-2-pyrrolidinone, formamide, dimethylformamide, acetonitrile, nitromethane, trimethyl phosphate, triethyl phosphate, trioctyl phosphate, and triester phosphate.

The above-listed nonaqueous organic solvents may be used alone or in a combination of at least two of the nonaqueous organic solvents. In the latter, a mixing ratio of the at least two nonaqueous organic solvents may be appropriately (or suitably) adjusted depending on a desired (or suitable) performance of the battery.

In some embodiments, the electrolyte may optionally further include an additional additive, in addition to the sulfonylmethylisocyanide-based compound of Formula 1 above, if suitable.

For example, the electrolyte may further include vinylene carbonate (VC), catechol carbonate (CC), or the like to form and maintain an SEI layer on the surface of the negative electrode.

In some other embodiments, the electrolyte may further include a redox-shuttle additive, for example, n-butyl ferrocene, a halogen-substituted benzene, or the like to prevent (or reduce) overcharging.

In some other embodiments, the electrolyte may further include a film-forming additive, for example, cyclohexyl benzene, biphenyl, or the like.

In some other embodiments, the electrolyte may further include a cation receptor, such as a crown ether-based compound, and an anion receptor, such as a boron-based compound, to improve conductive characteristics thereof.

In some other embodiments, the electrolyte may further include a phosphate-based compound as a flame retardant material, for example, trimethyl phosphate (TMP), tris(2,2,2-trifluoroethyl)phosphate (TFP), hexamethoxy cyclotriphosphazene (HMTP), or the like.

The electrolyte may further include an other additive to facilitate the formation of a stable SEI layer or film on the surface of an electrode to further improve the safety of the lithium battery, if suitable. Non-limiting examples of the other additive include tris(trimethylsilyl) phosphate (TM-SPa), lithium difluorooxalato borate (LiFOB), propane sultone (PS), succinonitrile (SN), $LiBF_4$, a silane compound having a functional group capable of forming a siloxane bond (for example, an acryl group, an amino group, an epoxy group, a methoxy group, an ethoxy group, or a vinyl group), a silazane compound (e.g., such as hexamethyl disilazane), and a combination thereof. For example, the other additive may include PS, SN, $LiBF_4$, or the like.

These other additives may be used alone or in a combination of at least two of the other additives.

For example, the above-listed cyclic carbonate compounds, for example, VC, FEC, or VEC, may be used as the other electrolyte additive.

An amount of any of the other additives, excluding the sulfonylmethylisocyanide-based compound of Formula 1 above, may be about 0.01 parts by weight to about 20 parts by weight based on 100 parts by weight of the nonaqueous organic solvent. For example, the amount of any of the other additives, excluding the sulfonylmethylisocyanide-based compound of Formula 1 above, may be about 0.05 parts by weight to about 15 parts by weight, and in some embodiments, about 0.1 parts by weight to about 10 parts by weight, and in some other embodiments, about 0.5 parts by weight to about 8 parts by weight, each based on 100 parts by weight of the nonaqueous organic solvent. However, the amount of the additional (or other) additive is not limited thereto, as long as it significantly does not reduce the capacity retention rate of the lithium battery including the electrolyte.

According to another embodiment of the present disclosure, a lithium battery includes a positive electrode, a negative electrode, and any of the above-described electrolytes. For example, the lithium battery may include a positive electrode including a positive active material, a negative electrode disposed opposite to the positive electrode (e.g., a negative electrode facing the positive electrode) and including a negative active material, a separator disposed between the positive and negative electrodes, and any of the electrolytes according to the above-described embodiments.

Any suitable lithium-containing metal oxide that is available in the art may be used as the positive active material. The positive active material may be at least one of a composite oxide of lithium with a metal selected from among nickel (Ni), cobalt (Co), manganese (Mn), and a combination thereof. For example, the positive electrode active material may be a compound represented by one of the following formulae: $Li_aA_{1-b}B_bD_2$ (where $0.90 \leq a \leq 1$, and $0 \leq b \leq 0.5$); $Li_aE_{1-b}B_bO_{2-c}D_c$ (where $0.90 \leq a \leq 1$, $0 \leq b \leq 0.5$, and $0 \leq c \leq 0.05$); $LiE_{2-b}B_bO_{4-c}D_c$ (where $0 \leq b \leq 0.5$, and $0 \leq c \leq 0.05$); $Li_aNi_{1-b-c}Co_bB_cD_\alpha$ (where $0.90 \leq a \leq 1$, $0 \leq b \leq 0.5$, $0 \leq c \leq 0.05$, and $0 < \alpha \leq 2$); $Li_aNi_{1-b-c}Co_bB_cO_{2-\alpha}F_\alpha$ (where $0.90 \leq a \leq 1$, $0 \leq b \leq 0.5$, $0 \leq c \leq 0.05$, and $0 < \alpha < 2$); $Li_aNi_{1-b-c}Co_bB_cO_{2-\alpha}F_2$ (where $0.90 \leq a \leq 1$, $0 \leq b \leq 0.5$, $0 \leq c \leq 0.05$, and $0 < \alpha < 2$); $Li_aNi_{1-b-c}Mn_bB_cD_\alpha$ (where $0.90 \leq a \leq 1$, $0 \leq b \leq 0.5$, $0 \leq c \leq 0.05$, and $0 < \alpha \leq 2$); $Li_aNi_{1-b-c}Mn_bB_cO_{2-\alpha}F_\alpha$ (where $0.90 \leq a \leq 1$, $0 \leq b \leq 0.5$, $0 \leq c \leq 0.05$, and $0 < \alpha < 2$); $Li_aNi_{1-b-c}Mn_bB_cO_{2-\alpha}F_2$ (where $0.90 \leq a \leq 1$, $0 \leq b \leq 0.5$, $0 \leq c \leq 0.05$, and $0 < \alpha < 2$); $Li_aNi_bE_cG_dO_2$ (where $0.90 \leq a \leq 1$, $0 \leq b \leq 0.9$, $0 \leq c \leq 0.5$, and $0.001 \leq d \leq 0.1$); $Li_aNi_bCo_cMn_dG_eO_2$ (where $0.90 \leq a \leq 1$, $0 \leq b \leq 0.9$, $0 \leq c \leq 0.5$, $0 \leq d \leq 0.5$, and $0.001 \leq e \leq 0.1$); $Li_aNiG_bO_2$ (where $0.90 \leq a \leq 1$, and $0.001 \leq b \leq 0.1$); $Li_aCoG_bO_2$ (where $0.90 \leq a \leq 1$, and $0.001 \leq b \leq 0.1$); $Li_aMnG_bO_2$ (where $0.90 \leq a \leq 1$, and $0.001 \leq b \leq 0.1$); $Li_aMn_2G_bO_4$ (where $0.90 \leq a \leq 1$, and $0.001 \leq b \leq 0.1$); $QO_2$; $QS_2$; $LiQS_2$; $V_2O_5$; $LiV_2O_5$; $LiIO_2$; $LiNiVO_4$; $Li_{(3-f)}J_2(PO_4)_3$ (where $0 \leq f \leq 2$); $Li_{(3-f)}Fe_2(PO_4)_3$ (where $0 \leq f \leq 2$); and $LiFePO_4$.

In the formulae above, A is selected from the group consisting of nickel (Ni), cobalt (Co), manganese (Mn), and combinations thereof; B is selected from the group consisting of aluminum (Al), nickel (Ni), cobalt (Co), manganese (Mn), chromium (Cr), iron (Fe), magnesium (Mg), strontium (Sr), vanadium (V), a rare earth element, and combinations thereof; D is selected from the group consisting of oxygen (O), fluorine (F), sulfur (S), phosphorus (P), and combinations thereof; E is selected from the group consisting of cobalt (Co), manganese (Mn), and combinations thereof; F is selected from the group consisting of fluorine (F), sulfur (S), phosphorus (P), and combinations thereof; G is selected from the group consisting of aluminum (Al), chromium (Cr), manganese (Mn), iron (Fe), magnesium (Mg), lanthanum (La), cerium (Ce), strontium (Sr), vanadium (V), and combinations thereof; Q is selected from the group consisting of titanium (Ti), molybdenum (Mo), manganese (Mn), and combinations thereof; I is selected from the group consisting of chromium (Cr), vanadium (V), iron (Fe), scandium (Sc), yttrium (Y), and combinations thereof; and J is selected from the group consisting of vanadium (V), chromium (Cr), manganese (Mn), cobalt (Co), nickel (Ni), copper (Cu), and combinations thereof.

For example, the positive electrode active material may be $LiCoO_2$, $LiMn_xO_{2x}$ (where x=1 or 2), $LiNi_{1-x}Mn_xO_{2x}$ (where $0<x<1$), $LiNi_{1-x-y}Co_xMn_yO_2$ (where $0 \leq x \leq 0.5$, and $0 \leq y \leq 0.5$), or $FePO_4$.

The compounds listed above as positive electrode active materials may have a surface coating layer (hereinafter, a "coating layer"). Alternatively, a mixture of a compound without a coating layer and a compound having a coating layer, the compounds being selected from the compounds listed above, may be used. The coating layer may include at least one compound of a coating element selected from the group consisting of oxide, hydroxide, oxyhydroxide, oxycarbonate, and hydroxycarbonate. The compounds for the coating layer may be amorphous or crystalline. The coating element for the coating layer may be magnesium (Mg), aluminum (Al), cobalt (Co), potassium (K), sodium (Na), calcium (Ca), silicon (Si), titanium (Ti), vanadium (V), tin (Sn), germanium (Ge), gallium (Ga), boron (B), arsenic (As), zirconium (Zr), or mixtures thereof. The coating layer may be formed using any suitable method that does not adversely affect the physical properties of the positive electrode active material when a compound of the coating element is used. For example, the coating layer may be formed using a spray coating method, a dipping method, or the like. This should be apparent to those of ordinary skill in the art, and thus further description thereof will not be reiterated here.

For example, the positive electrode may be manufactured by mixing such a positive active material, a binder, and optionally a conducting agent in a solvent to prepare a positive electrode slurry composition, and then molding the positive electrode slurry composition into a certain shape, or coating the positive electrode slurry composition on a current collector such as an aluminum foil.

The binder in the positive electrode slurry composition may facilitate binding between the positive active material and the conducting agent, and binding of the positive active material to the current collector. The amount of the binder in the positive electrode slurry composition may be about 1 to about 50 parts by weight based on 100 parts by weight of the total weight of the positive active material. For example, the amount of the binder in the positive electrode slurry composition may be about 1 part to about 30 parts by weight, in some embodiments, about 1 part to about 20 parts by weight, and in some embodiments, about 1 part to about 15 parts by weight, each based on 100 parts by weight of the positive active material. Non-limiting examples of the binder include polyvinylidene fluoride (PVDF), polyvinylidene chloride, polybenzimidazole, polyimide, polyvinyl acetate, polyacrylonitrile, polyvinyl alcohol, carboxymethyl cellulose (CMC), starch, hydroxypropyl cellulose, regenerated cellulose, polyvinylpyrrolidone, tetrafluoroethylene, polyethylene, polypropylene, polystyrene, polymethyl methacrylate, polyaniline, acrylonitrile butadiene styrene, phenol resin, epoxy resin, polyethylene terephthalate, polytetrafluoroethylene, polyphenylene sulfide, polyamide imide, polyether imide, polyethylene sulfone, polyamide, polyacetal, polyphenylene oxide, polybutylene terephthalate, ethylene-propylene-diene monomer (EPDM), sulfonated EPDM, styrene-butadiene rubber (SBR), fluoro rubber, and a combination thereof.

Optionally, the positive electrode may further include a conducting agent that provides a conduction path to the positive active material to further improve electrical conductivity thereof. The conducting agent may be any suitable one available for use in lithium batteries. Non-limiting examples of the conducting agent include carbonaceous materials, such as natural graphite, artificial graphite, carbon black, acetylene black, ketchen black, carbon fibers, or the like; metal-based materials, such as copper, nickel, aluminum, silver, or the like, in powder or fiber form; and conductive materials, including conductive polymers, such as a polyphenylene derivative; and a mixture thereof. The amount of the conducting agent may be appropriately (or suitably) adjusted. For example, a weight ratio of the positive active material to the conducting agent may be about 99:1 to about 90:10.

Non-limiting examples of the solvent include N-methylpyrrolidone (NMP), acetone, water and a combination thereof. An appropriate (or suitable) amount of the solvent may be used to easily coat the current collector.

The current collector may have a thickness of about 3 μm to about 500 μm. The current collector is not particularly limited, and may be formed of any suitable material as long as it has a suitable conductivity without causing chemical changes in a fabricated battery. Non-limiting examples of the material for forming the current collector include copper, stainless steel, aluminum, nickel, titanium, sintered carbon, copper or stainless steel that is surface-treated with carbon, nickel, titanium, or silver, and aluminum-cadmium alloys. In addition, the current collector for the positive electrode may be processed to have fine irregularities on surfaces thereof so as to enhance an adhesive strength thereof to the positive active material, and may be used in any of various suitable forms including films, sheets, foils, nets, porous structures, foams, and non-woven fabrics.

The positive electrode may be manufactured by directly coating the positive electrode slurry composition on an aluminum current collector to form a positive electrode plate and drying and pressing the positive electrode plate. Alternatively, the positive electrode may be manufactured by casting the positive electrode slurry composition on a separate support to form a positive active material film, separating the positive active material film from the support, laminating the positive active material film on an aluminum current collector to form a positive electrode plate, and drying and pressing the positive electrode plate.

The negative electrode may be manufactured in the same or substantially the same manner as the positive electrode, except for using a negative active material, instead of the positive active material. A binder, a conducting agent, and a solvent for a negative electrode slurry composition may be the same or substantially the same as those in the positive electrode slurry composition.

The negative electrode may be manufactured by directly coating the negative electrode slurry composition on a copper current collector to form a negative electrode plate, and drying and pressing the negative electrode plate. Alternatively, the negative electrode may be manufactured by casting the negative electrode slurry composition on a separate support to form a negative active material film, separating the negative active material film from the support, laminating the negative active material film on a copper current collector to form a negative electrode plate, and drying and pressing the negative electrode plate.

The negative active material may be any suitable negative active material for a lithium battery that is available in the art. For example, the negative active material may include at least one selected from the group consisting of lithium metal, a metal that is alloyable with lithium, a transition metal oxide, a non-transition metal oxide, and a carbonaceous material.

Non-limiting examples of the metal alloyable with lithium include Si, Sn, Al, Ge, Pb, Bi, Sb, a Si—Y alloy (where Y is an alkali metal, an alkali earth metal, a Group XIII element, a Group XIV element, a transition metal, a rare earth element, or a combination thereof except for Si), and a Sn—Y alloy (where Y is an alkali metal, an alkali earth metal, a Group XIII element, a Group XIV element, a transition metal, a rare earth element, or a combination thereof except for Sn). Y may be magnesium (Mg), calcium (Ca), strontium (Sr), barium (Ba), radium (Ra), scandium (Sc), yttrium (Y), titanium (Ti), zirconium (Zr), hafnium (Hf), rutherfordium (Rf), vanadium (V), niobium (Nb), tantalum (Ta), dubnium (Db), chromium (Cr), molybdenum (Mo), tungsten (W), seaborgium (Sg), technetium (Tc), rhenium (Re), bohrium (Bh), iron (Fe), lead (Pb), ruthenium (Ru), osmium (Os), hassium (Hs), rhodium (Rh), iridium (Ir), palladium (Pd), platinum (Pt), copper (Cu), silver (Ag), gold (Au), zinc (Zn), cadmium (Cd), boron (B), aluminum (Al), gallium (Ga), tin (Sn), indium (In), titanium (Ti), germanium (Ge), phosphorus (P), arsenic (As), antimony (Sb), bismuth (Bi), sulfur (S), selenium (Se), tellurium (Te), polonium (Po), or combinations thereof.

Non-limiting examples of the transition metal oxide include a lithium titanium oxide, a vanadium oxide, and a lithium vanadium oxide.

Non-limiting examples of the non-transition metal oxide include $SnO_2$ and $SiO_x$ (where $0<x<2$).

Non-limiting examples of the carbonaceous material include crystalline carbon, amorphous carbon, and mixtures thereof. Non-limiting examples of the crystalline carbon include graphite, such as natural graphite or artificial graphite in an amorphous, plate, flake, spherical, or fibrous form. Non-limiting examples of the amorphous carbon include soft carbon, hard carbon, meso-phase pitch carbides, sintered corks, and the like.

Next, a separator to be disposed between the positive electrode and the negative electrode is prepared. The positive electrode and the negative electrode may be separated from each other by the separator. Any suitable separator that is available for use with lithium batteries may be used. In an embodiment, the separator may have a low resistance to migration of ions in the electrolyte and a high electrolyte-retaining ability. Non-limiting examples of the separator include glass fiber, polyester, polyethylene, polypropylene, polytetrafluoroethylene (PTFE; e.g., TEFLON®), and a combination thereof, each of which may be a nonwoven fabric or a woven fabric. The separator may have a pore diameter of about 0.01 μm to about 10 μm and a thickness of about 5 μm to about 300 μm.

After forming an electrode assembly having a layer-built cell structure in which bicell structures having a structure of a positive electrode/a separator/a negative electrode/a separator/a positive electrode, or unit cell structures are repeatedly disposed upon one another, the electrode assembly may be encased in, for example, a cylindrical case, the electrolyte may be injected thereinto and a cap may be used to seal a lithium battery, and thus complete the manufacture of the lithium battery described above. The lithium battery, however, is not limited to the above-described embodiment.

A lithium battery 30 according to an embodiment of the present disclosure is illustrated in FIG. 1. Referring to FIG. 1, the lithium battery 30 includes a positive electrode 23, a negative electrode 22, and a separator 24 disposed between the positive electrode 23 and the negative electrode 22. The positive electrode 23, the negative electrode 22, and the separator 24 are wound or folded, and then accommodated in a battery case 25. Subsequently, an electrolyte is injected into the battery case 25, and the battery case 25 is sealed with a cap assembly member 26, thereby completing the manufacture of the lithium battery 30. The battery case 25 may have a cylindrical shape, a rectangular shape, or a thin-film shape. The lithium battery 30 may be a lithium ion battery.

Lithium batteries may be classified as either winding type (or winding kind) or stack type (or stack kind) depending on a structure of electrodes, or as either cylindrical type (or cylindrical kind), rectangular type (or rectangular kind), coin type (or coin kind), or pouch type (or pouch kind), depending on an exterior shape thereof.

Lithium batteries may be used as power sources for small devices and as unit cells for medium- or large-sized battery devices, each module of such batteries consisting of a plurality of unit cells.

Non-limiting examples of the medium- or large-sized devices include power tools; electric cars, including electric vehicles (EVs), hybrid electric vehicles (HEVs), plug-in hybrid electric vehicles (PHEVs); two-wheeled electric vehicles including E-bikes and E-scooters; electric golf carts; electric trucks; electric commercial vehicles, and power storage systems. In addition, the lithium battery may be used in any suitable applications that use a high-power output and high voltage, and also operate under high-temperature conditions.

The present invention will be described with reference to the following examples. These examples are for illustrative purposes only and are not intended to limit the scope of the present invention.

(Preparation of Electrolyte)

Preparation Example 1

After LiPF$_6$ was dissolved to a concentration of 1.3 M in a mixed nonaqueous organic solvent of ethylene carbonate (EC), ethylmethyl carbonate (EMC), and dimethyl carbonate (DMC) in a volume ratio of 10:10:80, 5 parts by weight of fluoroethyl carbonate (FEC), 0.5 parts by weight of vinylethylene carbonate (VEC), 1 part by weight of succinonitrile (SN), 0.2 parts by weight of LiBF$_4$, and 1 part by weight of p-toluenesulfonylmethyl isocyanide as a compound represented by Formula 4 below were added as additives thereto to prepare an electrolyte. The foregoing parts by weight were based on 100 parts by weight of the nonaqueous organic solvent.

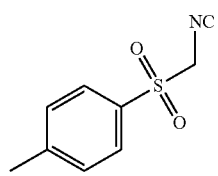

Formula 4

Preparation Example 2

An electrolyte was prepared as described with respect to Preparation Example 1, except that 1 part by weight of 1-allyl-1-tosylmethyl isocyanide as a compound represented by Formula 7 below was added as an additive instead of the p-toluenesulfonylmethyl isocyanide represented by Formula 4.

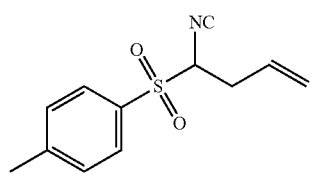

Formula 7

Preparation Example 3

An electrolyte was prepared substantially as described with respect to Preparation Example 1, except that 1 part by weight of 1-cyclopentyl-1-tosylmethyl isocyanide as a compound represented by Formula 8 below was added as an additive instead of the p-toluenesulfonylmethyl isocyanide represented by Formula 4.

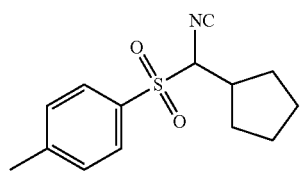

Formula 8

Preparation Example 4

An electrolyte was prepared substantially as described with respect to Preparation Example 1, except that 1 part by weight of 3-iodomethyl-1-[isocyano-(toluene-4-sulfonyl)-methyl]-benzene as a compound represented by Formula 10 below was added as an additive instead of the p-toluenesulfonylmethyl isocyanide represented by Formula 4.

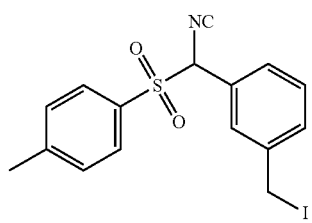

Formula 10

Preparation Example 5

An electrolyte was prepared substantially as described with respect to Preparation Example 1, except that 1 part by weight of 4-methoxy-1-[isocyano-(toluene-4-sulfonyl)-methyl]-benzene as a compound represented by Formula 11 below was added as an additive instead of the p-toluenesulfonylmethyl isocyanide represented Formula 4.

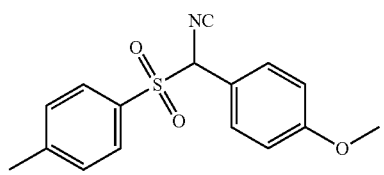

Formula 11

Preparation Example 6

An electrolyte was prepared substantially as described with respect to Preparation Example 1, except that 1 part by weight of 3-{Isocyano-[(4-methylphenyl)sulfonyl]methyl}pyridine as a compound represented by Formula 13 below was added as an additive instead of the p-toluenesulfonylmethyl isocyanide represented by Formula 4.

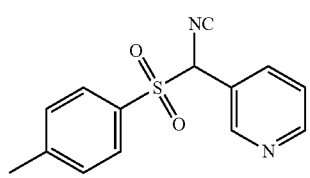

Formula 13

Preparation Example 7

An electrolyte was prepared substantially as described with respect to Preparation Example 1, except that 0.5 parts by weight of p-toluenesulfonylmethyl isocyanide as a compound represented by Formula 4 was added as an additive.

Preparation Example 8

An electrolyte was prepared substantially as described with respect to Preparation Example 1, except that 2 parts by weight of p-toluenesulfonylmethyl isocyanide as a compound represented by Formula 4 was added as an additive.

Comparative Preparation Example 1

An electrolyte was prepared substantially as described with respect to Preparation Example 1, except that p-toluenesulfonylmethyl isocyanide as a compound represented by Formula 4 above was not added.

Comparative Preparation Example 2

An electrolyte was prepared substantially as described with respect to Preparation Example 1, except that 1 part by weight of butyl isocyanide as a compound represented by Formula 14 below was added instead of the p-toluenesulfonylmethyl isocyanide represented by Formula 4.

Formula 14

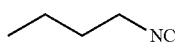

Comparative Preparation Example 3

An electrolyte was prepared substantially as described with respect to Preparation Example 1, except that 1 part by weight of difluoromethyl phenyl sulfone as a compound represented by Formula 15 below was added instead of the p-toluenesulfonylmethyl isocyanide represented by Formula 4.

Formula 15

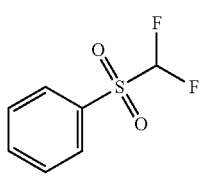

Comparative Preparation Example 4

An electrolyte was prepared substantially as described with respect to Preparation Example 1, except that 1 part by weight of 2-(pyridine-2-sulfonyl)ethylamine as a compound represented by Formula 16 below was added instead of the p-toluenesulfonylmethyl isocyanide represented by Formula 4.

Formula 16

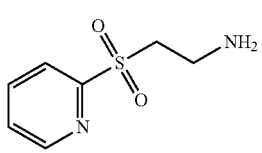

(Manufacture of Test Cells)

Example 1

(Manufacture of Positive Electrode)

$LiNi_{0.5}CO_{0.3}Mn_{0.2}O_2$ as a positive active material, polyvinylidenedifluoride (PVDF) as a binder, and denka black as a conducting agent were mixed in a weight ratio of 96:2:2. Then, N-methylpyrrolidone as a solvent was added thereto so that a viscosity of the mixture was controlled to have a solid content of 70% by weight, and thus a positive electrode slurry was manufactured.

An aluminum current collector having a thickness of about 15 μm was coated with the positive electrode slurry thus manufactured to a thickness of about 152 μm (when both surfaces of the current collector were coated, including the thickness of the current collector) by using a suitable coating method available in the art, dried at room temperature, dried again at a temperature of 120° C., and then pressed to manufacture a positive electrode.

(Manufacture of Negative Electrode)

Graphite (MSG-18) having an average particle diameter of about 17 μm as a negative active material, and styrene-butadiene rubber (SBR) and carboxymethylcellulose (CMC) as binders were mixed in a weight ratio of 97.5:1.5:1.0, and then distilled water as a solvent was added thereto so that a viscosity of the mixture was controlled to have a solid content of 48% by weight, and thus a negative electrode slurry was manufactured.

A copper current collector having a thickness of about 8 μm was coated with the negative electrode slurry thus manufactured to a thickness of about 152 μm (when both surfaces of the current collector were coated, including the thickness of the current collector) by using a suitable coating method available in the art, dried at room temperature, dried again at a temperature of 120° C., and then pressed to manufacture a negative electrode.

(Manufacture of Lithium Secondary Battery)

The positive electrode, the negative electrode, a double-layered polyethylene (PE) separator having a thickness of about 18 μm, and the electrolyte of Preparation Example 1 were used to manufacture a box-type (or box-kind; 2.1 Ah) battery.

Examples 2 to 8

Positive electrodes, negative electrodes, and lithium secondary batteries were manufactured substantially as described with respect to Example 1, except that the electrolytes of Preparation Examples 2 to 8 were used, respectively, instead of the electrolyte of Preparation Example 1.

Comparative Examples 1 to 4

Positive electrodes, negative electrodes, and lithium secondary batteries were manufactured substantially as described with respect to Example 1, except that the electrolytes of Comparative Preparation Examples 1 to 4 were used, respectively, instead of the electrolyte of Preparation Example 1.

Evaluation Example 1: Battery Safety Evaluation—Penetration Test

A penetration test was performed on the lithium secondary batteries of Examples 1 to 8 and Comparative Examples 1 to 4 as follows:

After the lithium secondary batteries were manufactured under a standard condition (charging at a constant current of 0.2 C to a charge cut-off voltage of 4.2V, left to rest for 10 minutes, discharging at a constant current of 0.2 C to a discharge cut-off voltage of 2.75 V, and then left to rest for 10 minutes), each of the batteries was subjected to be full-charged (charging at a constant current of 0.2 C to a charge cut-off voltage of 4.2 V). Then, each of the batteries was completely penetrated through the middle thereof with a nail (a 2.5-mm diameter) at a rate of about 80 mm/sec, and maintained until a surface temperature of the lithium secondary battery reached about 50° C. or less. The results of the penetration test are shown in Table 1 below.

TABLE 1

| | Safety evaluation | | |
|---|---|---|---|
| | 1$^{st}$ penetration | 2$^{nd}$ penetration | 3$^{rd}$ penetration |
| Example 1 | L1 | L1 | L4 |
| Example 2 | L1 | L1 | L1 |
| Example 3 | L1 | L1 | L1 |
| Example 4 | L1 | L1 | L1 |
| Example 5 | L1 | L1 | L1 |
| Example 6 | L1 | L1 | L1 |
| Example 7 | L1 | L1 | L1 |
| Example 8 | L1 | L1 | L1 |
| Comparative Example 1 | L4 | L4 | L4 |
| Comparative Example 2 | L4 | L4 | L4 |
| Comparative Example 3 | L4 | L4 | L4 |
| Comparative Example 4 | L4 | L4 | L4 |

*Battery Safety Evaluation Criteria
Table 1 legend:
L1: leakage,
L2: generation of heat of less than 200° C.,
L3: gas release,
L4: fire,
L5: bursting Referring to Table 1, the lithium secondary batteries of Examples 1 to 8 had improved safety, as compared to the lithium secondary batteries of Comparative Examples 1 to 4, indicating that an exothermic reaction was reduced in the lithium secondary batteries including the electrolytes to which the sulfonylmethylisocyanide-based compounds of Formula 1 were added, due to suppression (or reduction) of electrolyte decomposition.

On the other hand, the lithium secondary batteries of Comparative Examples 2 to 4, in which a compound having only either a sulfonyl group or an isocyanide group (but not both a sulfonyl group and an isocyanide group) were added to the electrolyte, decomposition of the additive did not occur faster than the electrolyte decomposition, and thus it may be understood that the stability of the lithium batteries of Comparative Examples 2 to 4 was not improved.

Evaluation Example 2: Evaluation of Charge-Discharge Characteristics

The lithium secondary batteries of Example 1 and Comparative Example 1 were each charged at a constant current of 0.2 C rate to a charge cut-off voltage of 4.2 V at about 25° C. Subsequently, the batteries were each discharged at a constant current of 0.2 C rate to a discharge cut-off voltage of 2.8 V to evaluate initial charge-discharge characteristics of the lithium secondary batteries. Differential charge/discharge curves at the first cycle of the lithium secondary batteries of Example 1 and Comparative Example 1 are shown in FIG. 2.

Figure 2:
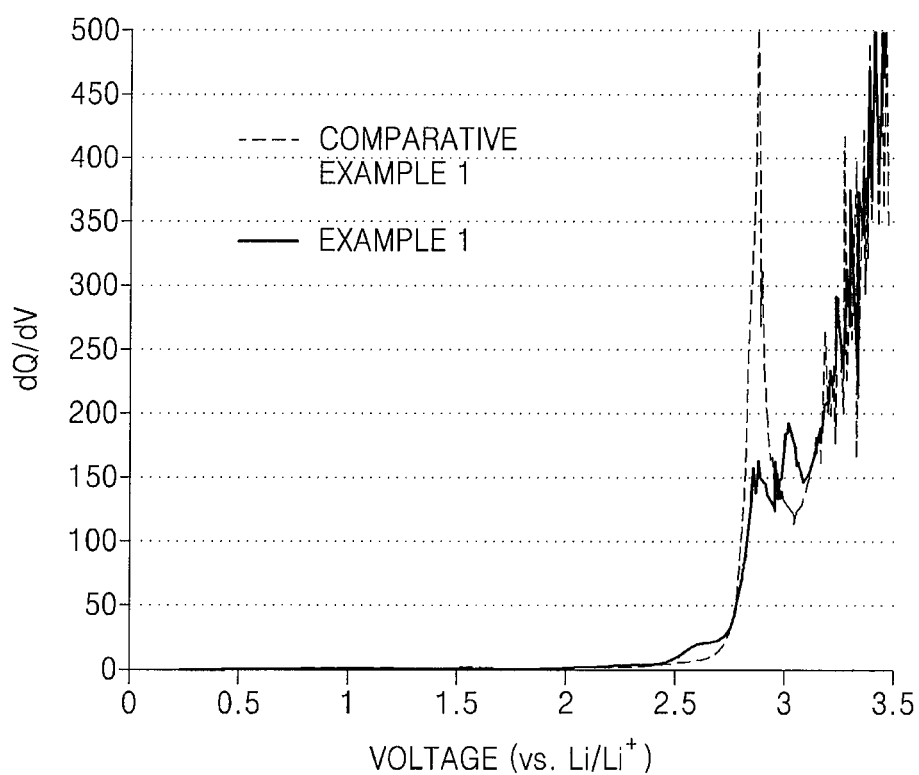
FIG. 2 is a graph of differential capacity (dQ/dV) curves of lithium batteries of Example 1 and Comparative Example 1.

Referring to FIG. 2, at a voltage of about 2.9 V, the lithium secondary battery of Comparative Example 1 exhibited a reduction peak of FEC in the solvent as used in the electrolytes of Examples 1 to 8 and Comparative Examples 1 to 4. In general, FEC reduces faster than EC, which is a non-aqueous organic solvent, and may prepare a stable SEI layer on a surface of a negative electrode.

On the other hand, the lithium secondary battery prepared as described in Example 1 exhibited a reduction peak of the SEI layer at about 2.7 V that is before about 2.9 V (e.g., is at a lower voltage than 2.9 V), at which the reduction peak of the lithium secondary battery of Comparative Example 1 was exhibited. The lithium secondary battery prepared as described in Example 1 had an additional reduction peak of FEC at about 2.9 V.

In this regard, it was determined that the additive, p-toluenesulfonylmethyl isocyanide, was reduced at a lower voltage than the nonaqueous organic solvent, and thus an SEI layer was formed in the lithium secondary battery prepared as described in Example 1 at lower voltage, as compared to that of the lithium secondary battery prepared as described in Comparative Example 1. For example, in the lithium secondary battery prepared as described in Example 1, decomposition of the electrolyte was suppressed (or reduced) due to reduction of the nonaqueous organic solvent, and thus it may be understood that safety of the lithium secondary battery prepared as described in Example 1 improved as a result.

Evaluation Example 3: Impedance Measurement

The impedances of the lithium secondary batteries of Example 1 and Comparative Example 1 were measured using an impedance analyzer (PARSTAT 2273) according to a 2-probe method. A frequency range for the impedance measurement was about 0.1 Hz to about 100,000 Hz. Nyquist plots obtained from the impedance measurement are shown in FIG. 3.

Figure 3:
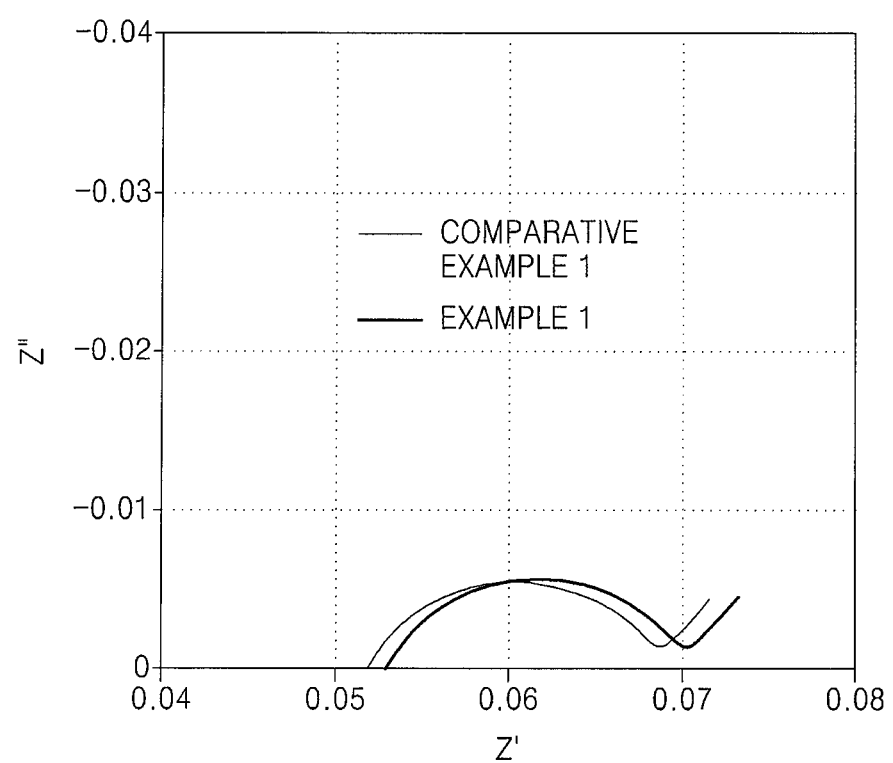
FIG. 3 is a graph of impedances of the lithium batteries of Example 1 and Comparative Example 1.

Referring to FIG. 3, the impedance of the lithium secondary battery of Example 1 increased due to formation of the SEI layer by the additive, p-toluenesulfonylmethyl isocyanide.

Evaluation Example 4: Battery Safety Evaluation—Thermal Runaway Reaction Experiment After each of the lithium secondary batteries of Example 1 and Comparative Example 1 was charged to 4.35 V at a state-of-charge (SOC) of 100%, temperature changes of the batteries were monitored using an accelerating rate calorimeter (ARC) while heating in an insulated state. ARC evaluation conditions are shown in Table 2 below.

TABLE 2

| Parameter setting | Set value |
|---|---|
| Start temperature | 25° C. |
| End temperature | 350° C. |
| Slope sensitivity | 0.02° C./min |
| Heat step temperature | 5° C. |
| Wait time | 15 minutes |
| Data step temperature | 1° C. |
| Data step time | 0.5 minutes |
| Calculation step temperature | 0.2° C. |

Figure 4:
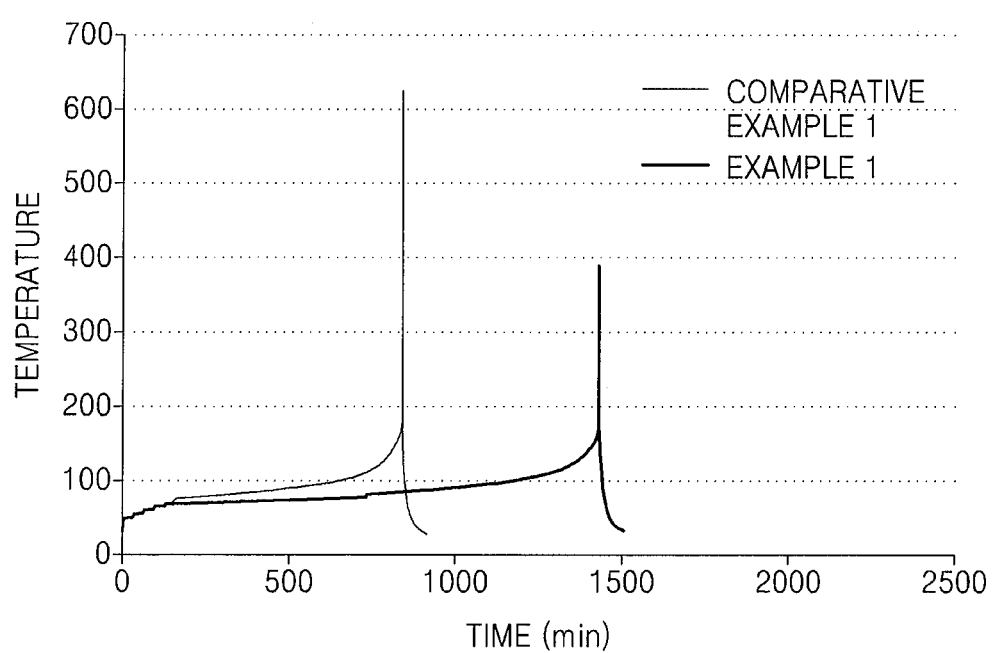
FIG. 4 is a graph of exothermic time of lithium batteries of Example 1 and Comparative example 1.

The results of the ARC evaluation are shown in Table 3 and FIG. 4.

TABLE 3

|  | Example 1 | Comparative Example 1 |
| --- | --- | --- |
| Cell weight (g) | 40.02 | 40.03 |
| Initial voltage (V) | 4.15 | 4.15 |
| On-set temperature (TO ° C.) | 66.1 | 68.6 |
| Self heat rate (° C./min) | 10.92 | 13.66 |
| Exothermic time (min) | 1436 | 843 |

Referring to Table 3 and FIG. 4, the lithium secondary battery prepared as described in Example 1 in which p-toluenesulfonylmethyl isocyanide was added to the electrolyte has a low self heat rate and a period of time for thermal runaway to occur that is twice as long as that of the lithium secondary battery prepared as described in Comparative Example 1. Thus, it was determined that addition of p-toluenesulfonylmethyl isocyanide to an electrolyte caused the formation of the SEI layer with improved high-temperature stability to suppress (or reduce) the occurrence of thermal runaway.

Evaluation Example 5: Life Characteristics Evaluation

The lithium secondary batteries prepared as described in Example 1 and Comparative Example 1 were charged at a constant current of 0.2 C rate at a temperature of about 25° C. until a voltage of the batteries reached a charge cut-off voltage of 4.2 V. Then, the batteries were discharged at a constant current of 0.2 C rate until a voltage of the batteries reached a discharge cut-off voltage of 2.8 V. 50 cycles including the charging and discharging process were performed on the batteries.

Figure 5:
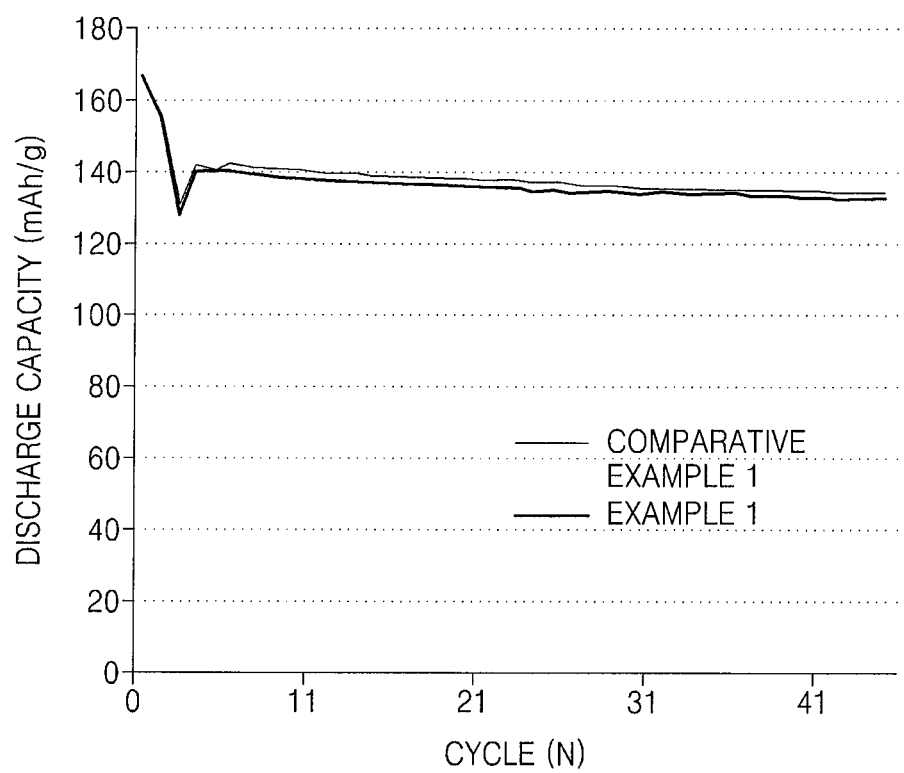
FIG. 5 is a graph of discharge capacities of the lithium batteries of Example 1 and Comparative example 1 per cycle.

A discharge capacity of each of the batteries was measured, and the results are shown in FIG. 5.

Referring to FIG. 5, although the impedance of the lithium secondary battery prepared as described in Example 1 was increased as compared to that of the lithium secondary battery prepared as described in Comparative Example 1, a decrease in the discharge capacity of the lithium secondary battery prepared as described in Example 1 was not observed. Thus, it was determined that when a sulfonylmethylisocyanide-based compound is added to an electrolyte, a stable SEI layer is formed on the negative electrode, and thus safety of the battery improves, but life characteristics of the battery are not deteriorated.

As described above, according to one or more of the above embodiments of the present invention, a lithium battery may include an electrolyte including a sulfonylmethylisocyanide-based compound as an additive. Consequently, the lithium battery may have improved safety due to suppressed (or reduced) exothermic reaction therein.

It should be understood that the exemplary embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the drawings, it will be understood by those of ordinary skill in the art that various changes in form and details may be made therein without departing from the spirit and scope of the present invention as defined by the following claims, and equivalents thereof.

What is claimed is:

1. An electrolyte for a lithium battery, the electrolyte comprising:
a lithium salt;
a nonaqueous organic solvent; and
an electrolyte additive comprising a sulfonylmethylisocyanide-based compound represented by Formula 1:

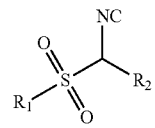

Formula 1 wherein, in Formula 1, $R_1$ is a substituted or unsubstituted C1-C20 alkyl group; a substituted or unsubstituted C1-C20 alkoxy group; a substituted or unsubstituted C2-C20 alkenyl group; a substituted or unsubstituted C2-C20 alkenyloxy group; a substituted or unsubstituted C4-C20 cycloalkyl group; a substituted or unsubstituted C4-C20 cycloalkenyl group; a substituted or unsubstituted C2-C20 alkynyl group; or a substituted or unsubstituted C6-C20 aryl group, and $R_2$ is a substituted or unsubstituted aliphatic, alicyclic, or aromatic hydrocarbon group,
wherein the substituted C1-C20 alkyl group; the substituted C1-C20 alkoxy group; the substituted C2-C20 alkenyl group; the substituted C2-C20 alkenyloxy group; the substituted C4-C20 cycloalkyl group; the substituted C4-C20 cycloalkenyl group; the substituted C2-C20 alkynyl group; the substituted C6-C20 aryl group, the substituted aliphatic hydrocarbon group, the substituted alicyclic hydrocarbon group, and the substituted aromatic hydrocarbon group are substituted with a substituent comprising:
a halogen atom; an amino group; a cyano group; a nitro group; a halogen-substituted or unsubstituted C1-C8 alkyl group; a halogen-substituted or unsubstituted C1-C8 alkoxy group; a halogen-substituted or unsubstituted C2-C8 alkenyl group; a halogen-substituted or unsubstituted C2-C8 alkenyloxy group; a halogen-substituted or unsubstituted C2-C8 alkynyl group; a halogen-substituted or unsubstituted C4-C10 cycloalkyl group; a halogen-substituted or unsubstituted C3-C10 cycloalkoxy group; a halogen-substituted or unsubstituted C4-C10 cycloalkenyl group; a halogen-substituted or unsubstituted C2-C10 heterocycloalkyl group; a halogen-substituted or unsubstituted C6-C10 aryl group; a halogen-substituted or unsubstituted C6-C10 aryloxy group; or a halogen-substituted or unsubstituted C6-C10 heteroaryl group, and
wherein an amount of the electrolyte additive in the electrolyte is about 0.01 parts to about 10 parts by weight based on 100 parts by weight of the nonaqueous organic solvent.

2. The electrolyte of claim 1, wherein the electrolyte further comprises at least one other additive selected from the group consisting of tris(trimethylsilyl) phosphate (TMSPa), lithium difluorooxalate borate (LiFOB), vinylene carbonate (VC), fluoroethylene carbonate (FEC), vinyl ethylene carbonate (VEC), propane sultone (PS), succinonitrile (SN), LiBF$_4$, a silane compound having a functional group able to form a siloxane bond, a silazane compound, and mixtures thereof.

3. The electrolyte of claim 1, wherein R$_1$ is a substituted or unsubstituted C6-C20 aryl group.

4. The electrolyte of claim 1, wherein the aliphatic hydrocarbon group of R$_2$ is a C1-C20 alkyl group, a C1-C20 alkoxy group, a C2-C20 alkenyl group, a C2-C20 alkenyloxy group; or a C2-C20 alkynyl group,
the alicyclic hydrocarbon group of R$_2$ is a C4-C20 cycloalkyl group; a C4-C20 cycloalkenyl group; or a C2-C20 heterocycloalkyl group, and
the aromatic hydrocarbon group is a C6-C20 aryl group or a C2-C20 heteroaryl group.

5. The electrolyte of claim 1, wherein R$_2$ is a hydrogen atom, a methyl group, an ethyl group, a propyl group, an isopropyl group, a butyl group, an isobutyl group, a tert-butyl group, a sec-butyl group, a vinyl group, an allyl group, a butenyl group, a pentenyl group, an ethynyl group, a propynyl group, a butynyl group, a pentynyl group, a cyclobutyl group, a cyclopentyl group, a cyclohexyl group, a cycloheptyl group, a phenyl group, a naphthyl group, a pyridinyl group, or a thiophenyl group.

6. The electrolyte of claim 1, wherein the sulfonylmethylisocyanide-based compound comprises a compound represented by Formula 3 below:

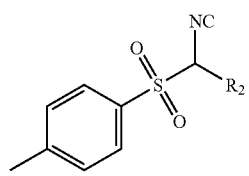

Formula 3 wherein, in Formula 3, R$_2$ is as defined with respect to Formula 1.

7. The electrolyte of claim 1, wherein the sulfonylmethylisocyanide-based compound comprises at least one of compounds represented by Formula 4 to Formula 13 below:

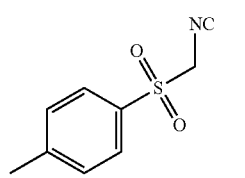

Formula 4

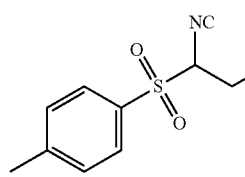

Formula 5

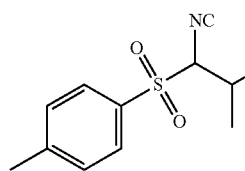

Formula 6

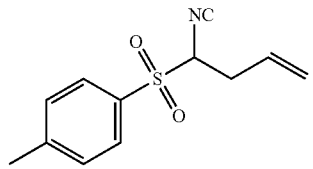

Formula 7

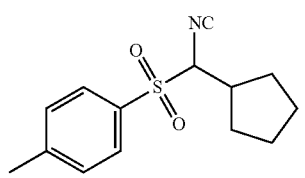

Formula 8

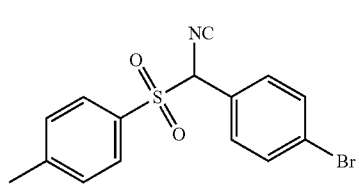

Formula 9

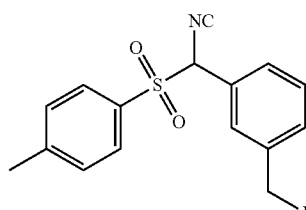

Formula 10

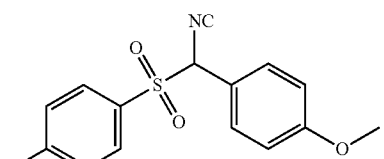

Formula 11

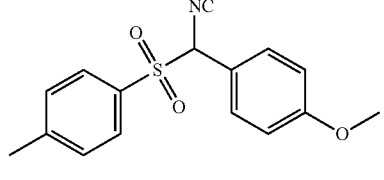

Formula 12

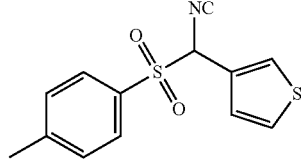

Formula 13

8. A lithium battery comprising:
a positive electrode;
a negative electrode; and
the electrolyte of claim 1.

* * * * *